United States Patent [19]
Elam

[11] Patent Number: 6,097,785
[45] Date of Patent: Aug. 1, 2000

[54] CONE PENETROMETER UTILIZING AN X-RAY FLUORESCENCE METALS SENSOR

[75] Inventor: William T. Elam, Alexandria, Va.

[73] Assignee: The United States of America as represented by the Secretary of the Navy, Washington, D.C.

[21] Appl. No.: 09/182,814

[22] Filed: Oct. 30, 1998

[51] Int. Cl.[7] .............................................. G01N 23/223
[52] U.S. Cl. ......................... 378/45; 250/253; 250/269.1
[58] Field of Search ................................ 250/253, 269.1; 378/45

[56] References Cited

U.S. PATENT DOCUMENTS

| | | | |
|---|---|---|---|
| 4,349,736 | 9/1982 | Miller | 378/46 |
| 4,510,573 | 4/1985 | Boyce et al. | 702/23 |
| 5,014,287 | 5/1991 | Thornton et al. | 378/45 |
| 5,128,882 | 7/1992 | Cooper et al. | 702/11 |
| 5,495,106 | 2/1996 | Mastny | 250/253 |
| 5,548,115 | 8/1996 | Ballard et al. | 250/253 |
| 5,635,710 | 6/1997 | Reed et al. | 250/253 |
| 5,739,536 | 4/1998 | Bucholtz et al. | 250/341.2 |
| 5,811,816 | 9/1998 | Gallagher et al. | 250/370.15 |

OTHER PUBLICATIONS

Elam et al., "Report on the Use of Fluorescence as a Trace Metal Sensor for the Cone Penetrometer", Naval Research Laboratory, NRL/MR/6685—94–7420, Feb. 28, 1994.
Aggarwal et al., *SPIE*, vol. 2367, 59–69 (1994).
Elam et al., *Advances in X–Ray Analysis*, vol. 38, ed. P. Predecki et al, Plenum Press, New York (1995) 699–704.
Elam et al., *Advances in X–Ray Analysis*, vol. 39, ed. J.V. Gilfrich et al, Plenum Press, New York (1997) 861–867.
A. C. Huber, J. A. Pantazis, and V. Jordanov. Nuclear Instruments and Methods in Physics Research B99, 665 (1995).
Elam et al., Field Analytical Chemistry and Technology 2, 97 (1998).
Elam et al., in Current Protocols in Field Analytical Chemistry, edited by Viorica Lopez–Avila (New York: John Wiley & Sons, Inc., 1998).
Elam et al., in Field Analytical Methods for Hazardous Wastes and Toxic Chemicals. 1997 Proceedings of a coference sponsored by the Air & Waste Management Association in Las Vegas, NV.

*Primary Examiner*—David P. Porta
*Assistant Examiner*—Allen C. Ho
*Attorney, Agent, or Firm*—Barry A. Edelberg; Ralph T. Webb

[57] ABSTRACT

A cone-tipped penetrometer for in situ analysis of soil or sediment by X-ray fluorescence spectroscopy. Rather than using a radioactive source, a miniature x-ray tube is powered by a filament isolation transformer located inside the penetrometer pipe which has an outside diameter of about 2 inches or less. The x-rays pass out through a special x-ray transmissive window, such as a low metal impurity-containing high strength boron carbide, into the soil or sediment below the surface and the resulting x-rays from the metals in the soil or sediment return through the window to a detector. The signal is transmitted back up to the surface where the x-rays are quantitatively analyzed to determine the concentration of metals in the soil. This real-time in situ x-ray fluorescence spectroscopy of soil or sediment samples permits field analysis of hazardous waste sites and other underground soil and underwater sediments.

18 Claims, 3 Drawing Sheets

CONE PENETROMETER UTILIZING AN X-RAY FLUORESCENCE METALS SENSOR

BACKGROUND OF THE INVENTION

1. Field of the Invention

This invention relates to a cone penetrometer which utilizes X-ray fluorescence spectroscopy to sense metals in soil or sediment samples underground.

2. Description of the Background Art

Previously, in situ analysis of soil, using a cone penetrometer, has been limited to reflectance and conventional fluorescence measurements.

U.S. Pat. No. 5,128,882 relates to a penetrometer unit which measures reflectance and fluorescence of in-situ soil. The probe is fitted with a light transparent window and a light source disposed internally of the probe. Light inside the probe passes through the window and is reflected back through the window from the soil as the probe passes through the soil. The light reflected from the soil back through the window is collected by a fiber optic link within the probe. The collected light is then transmitted through the fiber optic link to the surface for measurement and recordation of spectral distribution and intensity. Determination of the type and amount of contaminant is possible by comparison of the spectral signature of the soil to standards prepared by adding known concentrations of specific contaminant to soil similar to the soil found on the test site. It does not use U.S. Pat. No. 5,739,536 to Frank Bucholtz et al at NRL relates to a penetrometer which uses infrared. The penetrometer has a source for providing infrared radiation which passes through the window to irradiate the soil which is adjacent to the window and a spectrometer receives and analyzes the reflected infrared radiation passing back from the soil to obtain information on chemicals present at various depths of the soil through which the penetrometer passes. It does not use X-ray fluorescence.

While x-ray fluorescence spectroscopy of soil samples has occurred on-site, the soil samples had been removed from the ground before analysis.

U.S. Pat. No. 5,014,287 relates to a relatively large portable X-ray fluorescence spectrophotometer unit that is used for environmental monitoring of inorganic pollutants. This is a commercial device which is too large to fit into a penetrometer pipe.

U.S. Pat. No. 4,510.573 relates to performing X-ray fluorescence analysis on rock samples using an instrument which is inserted via a borehole and uses a radioactive source. The device is not suitable for direct insertion in soils via a penetrometer since it is not so designed, since it contains radioactive material and since it does not have a rugged window. The device performs a mineral assay by drilling a borehole into the rock matrix, inserting into the borehole a probe containing a suitable XRF source/detector, irradiating the matrix, detecting the spectrum of radiation that is produced and analyzing this spectrum. The rugged window, which is a critical part of the present invention, is not necessary in this device. FIG. 2 shows a torpedo shaped device which is described in col. 5, lines 58–68, as having a diameter of 1.5 inches and a length of 33 inches.

SUMMARY OF THE INVENTION

Accordingly, it is an object of this invention to provide a compact size x-ray fluorescence spectroscopy device which is self contained and can be employed below the ground to make subsurface measurements utilizing a variety of underground access techniques such as the cone penetrometer.

It is a further object of this invention to provide a cone penetrometer for in situ analysis of soil or sediment which is not limited to reflectance and conventional fluorescence measurements where the samples have to be removed from the ground before analysis.

It is a further object of this invention to provide for a cone penetrometer which permits the real-time in situ x-ray fluorescence spectroscopy of soil or sediment samples.

It is a further object of this invention to provide for a cone penetrometer which permits the mapping of mineral deposits, metal salts and other soil or sediment components by using x-ray fluorescence spectroscopy.

It is a further object of this invention to provide a cone penetrometer for in situ analysis of soil or sediment which uses no cryogenic cooling systems and no radioactive source.

It is a further object of this invention to provide a cone penetrometer for in situ analysis of soil or sediment which is compact enough to be pushed directly underground without drilling and which leaves no hazardous or radioactive contaminants if lost below ground.

It is a further object of this invention to provide a cone penetrometer for in situ analysis of soil or sediment which allows in-situ measurements without disturbing the soil or sediment from its natural environment and without taking samples which may not be representative of the subsurface conditions.

It is a further object of this invention to provide a cone penetrometer for in situ analysis of soil or sediment which allows data to be collected and analyzed in real time, accelerating assessment of subsurface conditions and providing information for directing analysis efforts while the site analysis is being conducted.

It is a further object of this invention to utilize a cone penetrometer for underwater sediment material in addition to soils.

These and further objects of the invention will become apparent as the description of the invention proceeds. A cone tipped penetrometer has been developed for in situ analysis of soil or sediment by X-ray fluorescence spectroscopy. The cone penetrometer is in the form of a pipe with an outside diameter of about 2 inches or less and inside there are four components. They are a miniature x-ray tube which does not use a radioactive source; a filament isolation transformer for transmitting heating power to the x-ray source across an insulating gap while allowing the source of the heating power to remain at a safe and practical potential with respect to the ambient; an x-ray transmissive window in the penetrometer pipe for the transmission of X-rays having a metal impurity content of less than 300 ppm and a yield strength so that it can withstand 250 lb/in$^2$ force on a ¼ inch diameter window; and a detector employing a solid state electrical diode for detecting the returning x-rays and for generating an electrical signal pulse for each x-ray whose amplitude is proportional to the energy of the x-ray. The x-ray transmissive window is made exclusively of materials with an atomic number of 6 or below and preferably of boron carbide.

The penetrometer is used with a system for real time in situ analysis of soil or sediment by x-ray fluorescence spectroscopy by connecting this cone penetrometer with all these components to an x-ray power supply which supplies power to the x-ray source. A further last component of the system is a quantitative analytical device for the detected x-rays. In the preferred embodiment the quantitative analytical device is made up of an electronic device for the detector to separate the pulses from the x-ray detector corresponding to each individual x-ray and to establish the correspondence between pulse height and energy of the x-ray; a multichannel analyzer for converting the pulses from the x-ray detector into a spectrum of x-rays as a function of energy; and a spectrum analysis and display device for separating the x-rays emitted by the metals in the soil or sediment from the remainder of the spectrum, quantifying these x-rays, and relating this quantity to the concentration of metals in the soil or sediment with reference to known calibration samples and display of the results for an operator. The electronic device for the detector has additional equipment for providing necessary voltages and currents for proper detector operation.

The method of operation for in situ analysis of soil or sediment by x-ray fluorescence spectroscopy is performed by inserting the cone penetrometer into the soil or sediment to be analyzed below the surface. Power is applied to the x-ray source to generate x-rays which pass out through the x-ray transmissive window and it causes x-rays to return back through the window. The returning x-rays are detected with a detector in the penetrometer and the signal is transmitted to above the surface. There the detected x-rays are quantitatively analyzed to determine the concentration of metals in the soil. This method permits the real-time in situ x-ray fluorescence spectroscopy of soil or sediment samples and it is useful for field analysis of hazardous waste sites and other underground soil and underwater sediment evaluations.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

Figure 1:
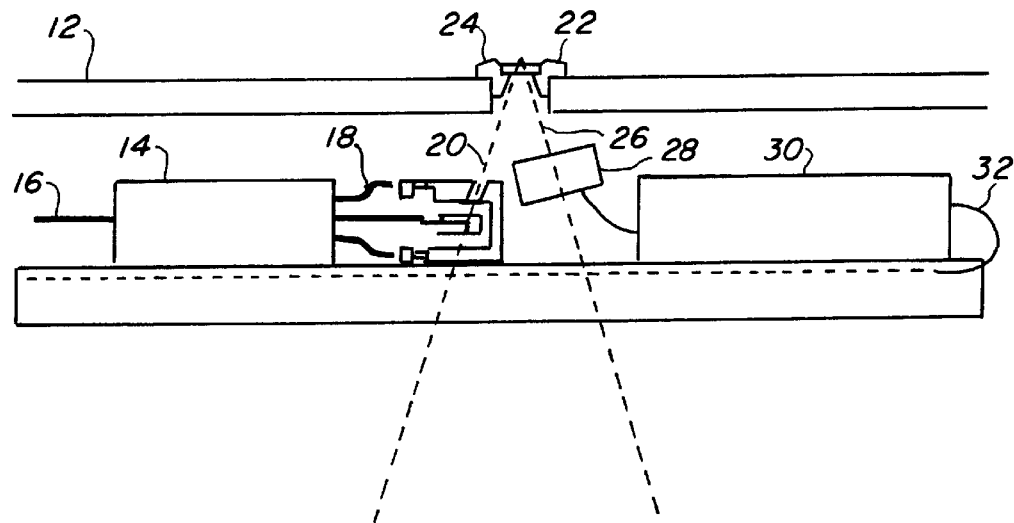
FIG. 1 is a sectional view of the sensing portion of the penetrometer around the window.

The key functioning section of the penetrometer apparatus is seen in FIG. 1. The penetrometer pipe 12 is a tube which contains the apparatus, provides sufficient strength to allow the device to be hydraulically pushed into the soil, and is small enough to avoid prohibitive resistance from the soil or sediment displacement. These pipes are typically less than about two inches outer diameter and have an inside diameter of about one and one-quarter inch. The pipe is preferably made of hardened steel. Within the pipe is an x-ray source 18. This is a sealed, evacuated x-ray tube which uses a source of electrons accelerated to high energies (at least 30,000 electron volts) by a large electrical potential to produce x-rays by striking a suitable target such as molybdenum, tantalum, or tungsten. Since the probe is occasionally lost below ground, a radioactive source is not appropriate for this application. Connected to the x-ray tube is the filament isolation transformer 14 which is used to provide the necessary power for the electron source, which is typically a thermionic or other type of electron emitter. The emitter must be heated to suitable temperature or otherwise supplied operating power to emit electrons, and the accelerating potential must be applied to the emitter. The filament isolation transformer provides a means of transmitting operating power to the emitter across an insulating gap which allows the source of the heating power to remain at a safe and practical potential with respect to the ambient. The small size required by the inside diameter of the penetrometer pipe places severe constraints on the geometry, arrangement, and high voltage insulation for the x-ray source and filament isolation transformer and prevents the use of any commercially available units. Cable 16 from the x-ray power supply up on the surface provides the power to the filament isolation transformer 14 and the accelerating potential to the x-ray tube.

The x-rays from the source 18 travel in an incident beam path 20 through a strong, x-ray transmissive window 22 and out to the soil or sediment sample pressing against the window. Any material with atomic number below 6 (i.e., below nitrogen in the Periodic Table) can be used if it has the requisite strength. The preferred window composition material is boron carbide because it is strong and because it allows the x-rays to pass from the x-ray source into the soil or sediment outside the penetrometer pipe and then it allows the x-ray signals from the metals in the soil or sediment under investigation to pass back inside the pipe to the x-ray detector. The penetrometer pipe is not transparent to x-rays in the energy range suitable for exciting the metals or that produced by the metals in the soil or sediment and thus a special window must be provided. The window must also be able to withstand the pressure of the soil or sediment displacement and the soil or sediment abrasion as the pipe is pushed into the soil. Finally, the window must not produce any x-rays which interfere with the signal from the metals under investigation. The window holder 24 holding the window 22 must withstand the pressures from the soil or sediment displacement while holding the window securely. It must not produce signals which interfere with the metals being investigated.

The returning x-rays from the soil or sediment return along a fluorescence beam bath 26 to an X-ray detector 28 which is a miniature, Peltier-cooled, energy-dispersive solid-state detector which provides electrical pulses whose amplitude is proportional to the energy of the detected x-ray. Peltier cooling involves passing a current across a junction of two metals of the correct type, so that one side becomes cold and the other side becomes hot. See CRC Handbook of Chemistry and Physics, Robert C. Weast and Melvin J. Astle Eds., 62nd Edition (CRC Press, Boca Raton) 1981, p. F-108 which formally defines the Peltier effect as occurring when a current flows across the junction of two unlike metals so that it gives rise to an absorption or liberation of heat. If the current flows in the same direction as the current at the hot junction in a thermoelectric circuit of the two metals, heat is absorbed; if it flows in the same direction as the current at the cold junction of the thermoelectric circuit heat is liberated. A detector preamp 30 amplifies this signal which is sent via cable 32 to the surface to the detector electronics.

Figure 2:
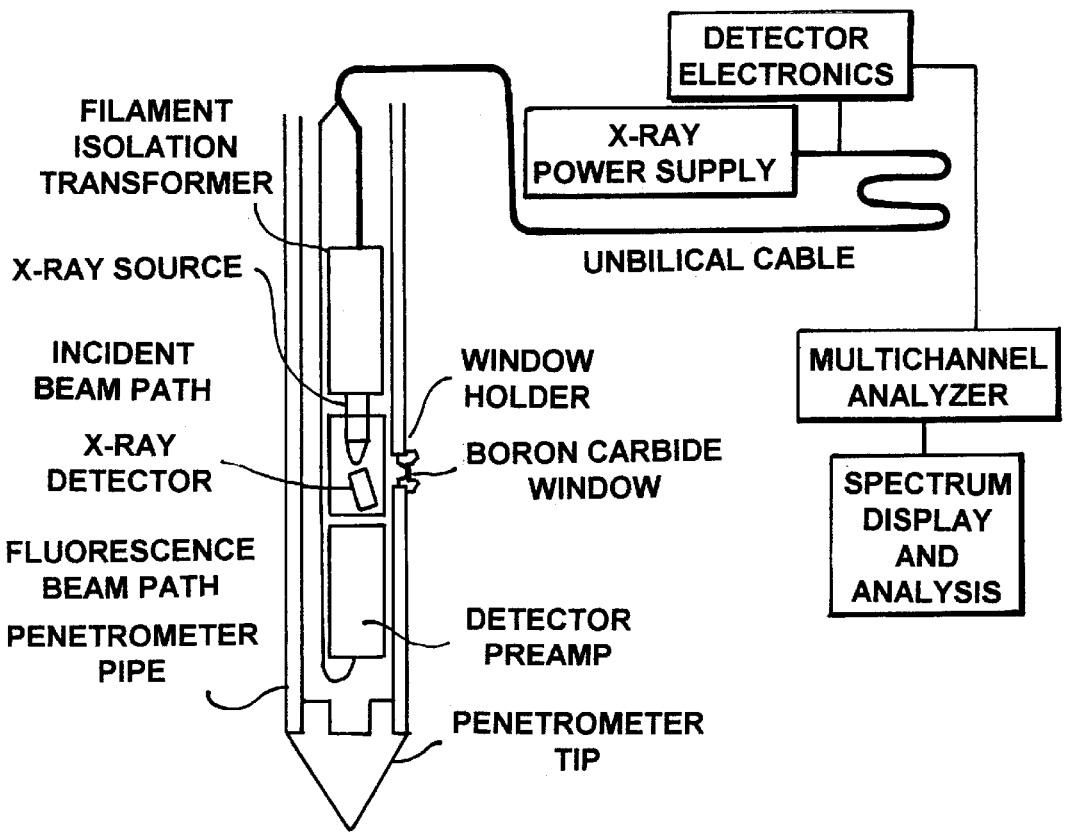
FIG. 2 is a schematic diagram of the various components of the penetrometer system.
Figure 3:
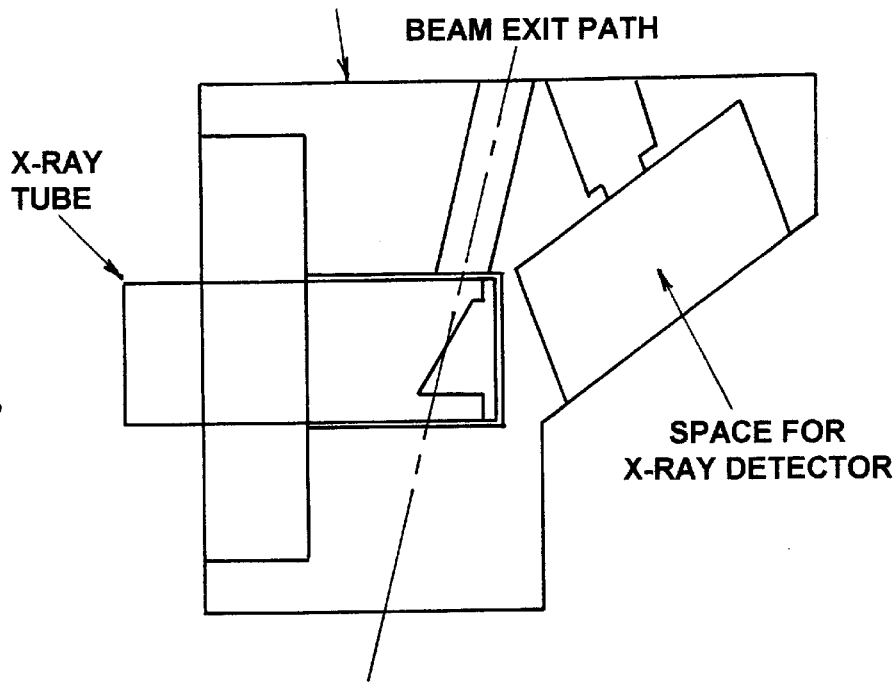
FIG. 3 is a section view of the x-ray tube and the detector.

FIG. 2 illustrates a schematic view of the entire system and includes the components above the ground. The penetrometer part is shown on the left and includes the penetrometer tip which improves the ability of the device to penetrate the soil or sediment and is a cone shaped block of hardened steel similar to the penetrometer pipe.

On the right side are the four major components of the system on the surface. The x-ray power supply provides the voltages and currents necessary to operate the x-ray source. It is constructed from conventional electronic components according to the established design methods and it supplies the power and accelerating potential down to the filament isolation transformer 14 and x-ray source 18 as shown in FIG. 1. The umbilical cord connected to the penetrometer has an electrical line from the detector preamp 30 in the penetrometer 10 to the quantitative analytical device which has as its first component the detector electronics. This detector electronics component is necessary to separate the pulses from the x-ray detector corresponding to each individual x-ray and to establish the correspondence between pulse height and energy of the x-ray. In addition, it provides the necessary voltages and currents for proper detector operation. It is typically supplied by the manufacturer of the detector.

Then the remaining parts of the quantitative analytical device for the detected x-rays includes a multichannel analyzer which converts the pulses from the x-ray detector into a spectrum of x-rays as a function of energy. Finally, the spectrum analysis and display component of the qualitative analytical device provides for the analysis of the x-ray spectrum from the soil or sediment by separating the x-rays emitted by the metals in the soil or sediment from the remainder of the spectrum, quantifying these x-rays, and relating this quantity to the concentration of metals in the soil or sediment with reference to known calibration samples and displaying the results for an operator and this is typically performed on a suitable portable computer according to the principles established for x-ray fluorescence spectroscopy.

In operating the system the preferred sensor performance requirements start with the ability to detect all metals typically found in environmentally contaminated sites, which includes almost all metals with atomic number greater than 20 (that is, all metals above calcium in the Periodic Table). These metals must be detectable at concentrations below the level of 100 parts per million by weight. These requirements must be met with a 100 second data collection time with no undue impact on the penetrometer speed of operation.

The x-ray source is preferably a sealed x-ray tube which uses a thermionic emitter or other source of electrons which are accelerated to an energy of at least 30,000 electron volts and strike an anode to produce x-rays. Since the probe is occasionally lost below ground, a radioactive source is not appropriate for this application. The x-rays from the anode are used to excite the metal atoms in the soil or sediment which causes them to emit characteristic x-rays. To allow the x-rays to exit from the penetrometer pipe while leaving sufficient room for the other components to receive and detect the emitted x-rays, the x-ray tube must emit x-rays in a specific direction and within specific narrow dimensions. Based on the required rigid specifications for the x-ray tube in this unique penetrometer configuration, a commercial supplier has been able to construct an acceptable x-ray tube for use in this device.

Figure 4:
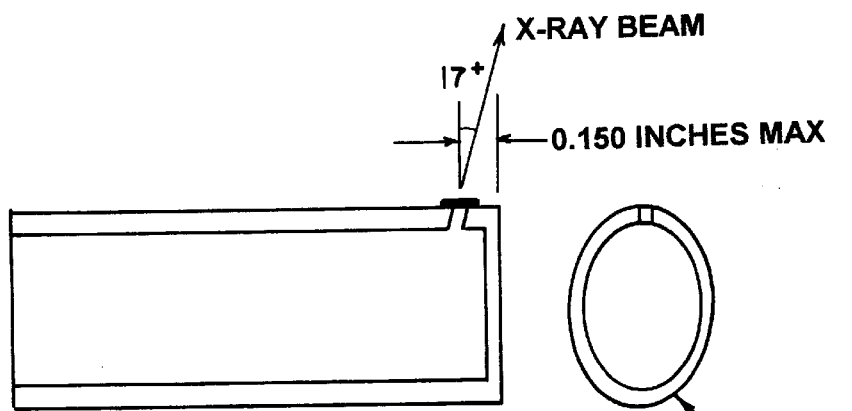
FIG. 4 is a sectional view of the x-ray tube and the end view showing it circular configuration.
Figure 5:
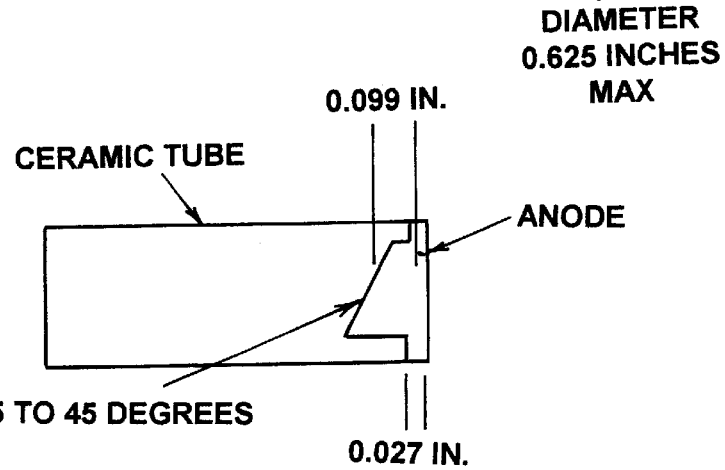
FIG. 5 is a portion of the x-ray tube and the anode.

Those specifications include (a) having a small enough size to be placed within the pipe which is preferably less than 0.625 inch diameter as illustrated in FIG. 4, (b) having a tube construction that the x-rays are emitted within about 0.150 inch from the end of the x-ray tube as illustrated in FIG. 4, and (c) having the x-rays emitted at an angle of preferably about 17 degrees as shown in FIG. 4. In FIG. 5 the angle of the anode is shown to be about 25 to 45 degrees to provide advantageous emission at about 17 degrees. An x-ray tube which met these constraints was not commercially available when the penetrometer was being designed, but as indicated above commercial suppliers have since been able to, upon our request, meet our design parameters and construct the required tube. These commercial suppliers of x-ray tubes are X-ray and Specialty Instruments, Inc., P.O. Box 3707, Ann Arbor, Mich. 48106, and ARPES Electronics, 634 Redwood Road, Felton, Calif. 95018.

The x-ray source must produce x-rays with energies of at least 30,000 electron volts in order to excite the metals in the soil. Producing these energetic x-rays requires electrons accelerated to 30,000 volts by a high voltage applied to the electron emitter. The accelerating potential is the voltage which accelerates the electrons from the emitter to give them enough energy to produce x-rays. It provides the power which actually operates the x-ray tube. The electron emitter must be supplied by a separate source of power in order to emit the required electrons. The filament isolation transformer transmits the power necessary to operate the electron emitter while allowing the accelerating potential (typically 30,000 to 50,000 volts) to be applied to the emitter to accelerate the emitted electrons. The isolation aspect of the transformer provides an insulating gap between the primary source of power and the secondary operating circuit in the electron emitter while retaining the power transmission. The insulating gap allows the source of the emitter power and the conductors which carry it through the cable to the device under the soil or sediment surface to remain at the ambient potential. This allows a practical means of constructing the emitter power source and provides for safe operation of the cables and power supply. Such a transformer which is able to withstand over 30,000 volts is not commercially available in this small size. The filament isolation transformer for the subject device was constructed using a powered ferrite core to avoid the heating effects of magnetic saturation and retain the efficient power transfer across the insulating gap. The secondary was wound with 26 gauge wire for low resistance and to provide mechanical support to allow the insulated secondary winding to be suspended within the insulating gap. The insulating gap was filled with a commercial silicone insulating compound which can withstand at least 400 volts per mil. The insulating compound was placed in an evacuated chamber to remove all air bubbles, which can destroy the insulation in the very small insulating gap in this device. The insulating gap is typically 0.1 inch.

The x-ray fluorescence device operates by detecting characteristic x-rays emitted by the atoms in the soil. The x-ray source bombards the soil or sediment with incident x-rays, where the atoms are excited. An incident x-ray excites an electron from a core level near the center of the atom to an empty state above the atomic states. The incident x-ray can have any energy which is greater than the binding energy of the core electron in the atom being excited. The empty core state is refilled by an electron from a higher energy state in the atom, producing a fluorescence x-ray. Since the electron energy states producing the fluorescence x-ray are entirely within the atom, the x-ray is produced with a constant and well-known energy (different for each type of atom). The excitation of core states (unlike the valence states used in atomic and optical spectroscopy) implies that the fluorescence x-rays have relatively high energies and are independent of the chemical state of the atoms. The relatively high energy of the x-rays makes them penetrate any type of matter for distances of several microns to several millimeters, regardless of optical transparency. Any type of atom with sufficiently energetic core levels can be detected in any matrix.

The characteristic x-rays are detected by an electronic detector which produces a pulse for each x-ray. The amplitude of the pulse is proportional to the x-ray energy, thus allowing the x-ray to be identified as to the metal atom which produced it. Adjacent metals produce characteristic x-ray energies which are typically 400 electron volts separated in energy. Thus the detector must be capable of resolving x-rays which have an energy difference of less than about 300 electron volts to adequately identify metals in soils. The number of x-rays produced will be related to the amount of the subject metal in the soil.

The relation between the number of x-rays detected and the concentration of a particular metal in the soil or sediment depends on the atomic properties of the metal atoms as mentioned above and the transmission of the metal's characteristic x-rays by the soil or sediment matrix. Since the soil or sediment composition may not be well known, methods for compensating for matrix effects must use information from the XRF spectrum as much as possible. This includes the effects of the metals being measured by XRF, since they can affect the matrix absorption if concentrations are large. The scattering of the incident x-rays by the sample also produces a characteristic pattern which depends on the average atomic number and can be used to produce fairly accurate matrix corrections. See Kirk K. Nielson, "Matrix Corrections for Energy Dispersive X-ray Fluorescence Analysis of Environmental Samples with Coherent/Incoherent Scattered X-rays", Analytical Chemistry 49 (April 1977), pp 641–648. The effects from the matrix seldom exceed 50 to 100% if the matrix is not too dissimilar from the standards used in calibration of the device. Accuracies of 1% or better are typical for analytical work with a full complement of carefully chosen standards. See L. S. Birks, X-ray *Spectrochemical Analysis*, Interscience (New York. 1959) p 69.

The lower detection limits for a particular type of metal depend on the efficiency with which it produces characteristic x-rays (a fundamental physical property of the atom), the transmission of x-rays by the surrounding soil, and the apparatus (including any materials in the beam path and the geometry), the x-ray source intensity, and the detector efficiency.

The x-rays used for exciting the metals in the soil or sediment and the characteristic x-rays from the metals pass out of and back into the device through an x-ray transparent window. This window also keeps the soil or sediment out of the device and must withstand the rigors of being pushed into the soil. It must also avoid producing any x-rays which would interfere with detecting the desired characteristic x-rays from metals in the soils. For x-ray transparency the window must be constructed of a material with low atomic number. For strength, the material must be dense and free of voids in addition to having sufficient strength in its atomic bonds. Boron carbide consists of boron with atomic number five and carbon with atomic number 6, meeting the low atomic number requirement. To achieve the necessary density, a sintering aid is typically used, such as iron. To avoid producing interfering x-rays, the window must not contain any metal impurities above a certain amount. This amount has been determined for this device by trial and error to be 300 parts per million by weight for iron and is similar for all other metals. To withstand being pushed into the soil, the window must have a yield strength sufficient to withstand 250 lbs/in$^2$ over a diameter of ¼ inch. This diameter provided the geometrical requirements necessary to achieve the performance outlined above. Boron carbide has a yield strength of 3200 pounds per square inch, which meets the strength requirement when sufficiently dense. The boron carbide must be manufactured using a hot-press method without any addition of sintering aids and must be carefully selected on the basis of impurity content to achieve the required yield strength without exceeding the maximum level of iron or other metal impurities.

The window is secured in a holder which has a low thermal coefficient of expansion (less than 6 parts per million per degree Celsius) to avoid damage to the boron carbide window, and the holder does not produce any characteristic x-ray which would interfere with the metals being examined in the soil. It must also be sufficiently durable to withstand being pushed into the soil. Molybdenum meets these requirements and it is a preferred holder material.

The monitoring unit is housed inside a pipe with sufficient strength to allow the unit to be pushed directly into the soil. This eliminates any requirement for drilling a borehole and the associated waste, sample extraction, and time. Highway accessibility limits the weight of a truck to 20 tons, which limits the available force to push the device. This in turn limits the diameter of the pipe to that which can be routinely pushed by 20 tons of force. The practical limits for pipe diameter under these constraints is about 2 inches, with a smaller pipe being useful under more varied conditions. The pipe must also be strong enough to withstand being pushed, which forces a thick wall and thus a smaller inside diameter. The largest practical inner diameter is about one and one-quarter inch. The x-ray fluorescence sensor components must fit within this diameter, which imposes severe constraints on the construction, especially for the high voltage isolation.

The voltages and currents required for operation of the underground components are carried down to the device via suitable cables. The voltages and currents are produced above ground by electronic modules constructed from conventional electronic components according to established design methods. The electrical pulses from the detector are amplified and filtered, then subjected to pulse height analysis in a conventional multichannel analyzer as known in x-ray detecting instruments. An example of a commercial unit is the Model MCA-8000 by AmpTek, Inc. The multichannel analyzer produces a spectrum of x-ray events as a function of the x-ray energies. This spectrum contains peaks at the characteristic emission energies of any metals present above the detection limits in the soil or sediment as discussed above.

Figure 6:
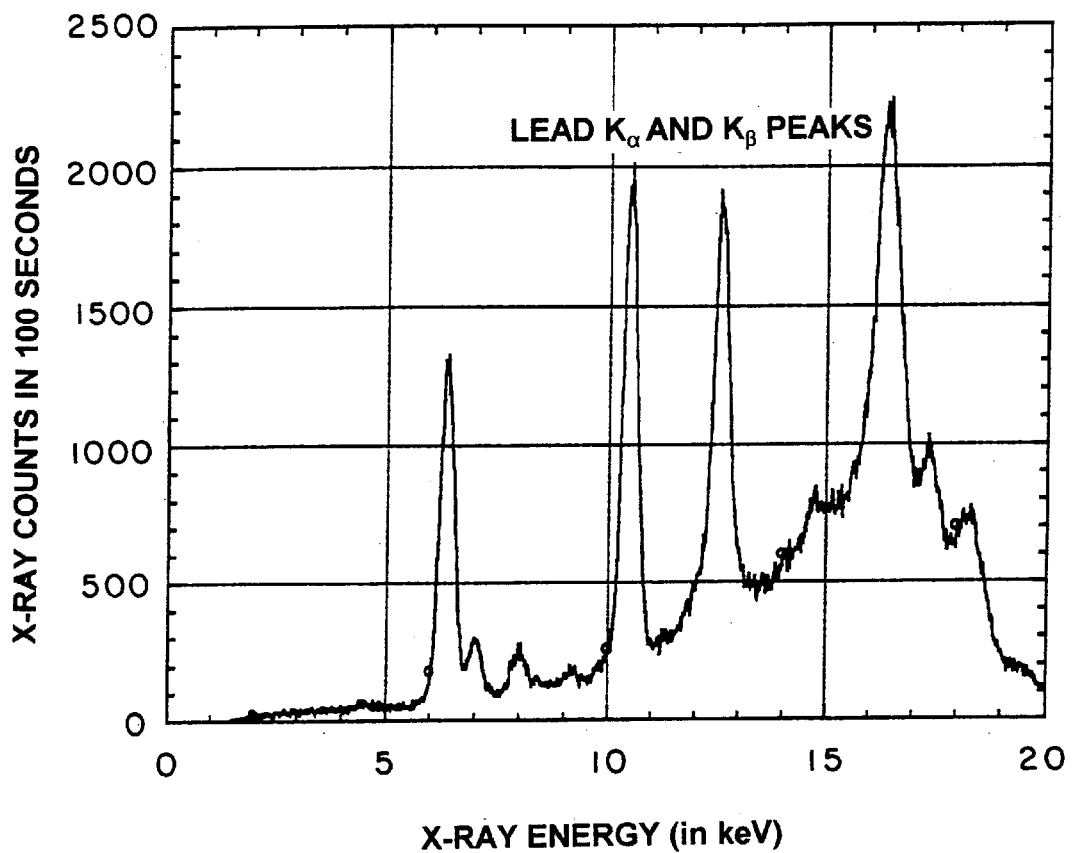
FIG. 6 is a spectrum taken while the device was 4.5 feet underground.

A spectrum taken while the device was 4.5 feet underground is shown in FIG. 6. Note the clear peaks from the lead which was a contaminant in the soil. The relation of the peak intensities to metal concentration in parts per million by weight is established using standards with known concentrations of the metals if interest. This relationship is used with data from an unknown soil or sediment to determine the amount of metal present. Such analysis can be performed, for example, during operation of the device immediately subsequent to collection of the spectrum. A suitable portable computer can be used to aid in this analysis and to display the results in a desirable form.

It is understood that the foregoing detailed description is given merely by way of illustration and that many variations may be made therein without departing from the spirit of this invention.

What is claimed is:

1. A cone tipped penetrometer for in situ analysis of a concentration of at least one metal in soil or sediment by X-ray fluorescence spectroscopy, comprising:
   a) a cone penetrometer having a pipe with an outside diameter of about 2 inches or less, said pipe having a longitudinal axis;
   b) a miniature x-ray tube within the penetrometer pipe having a diameter of less than about 0.625 inch which does not use a radioactive source;
   c) a filament isolation transformer within the penetrometer pipe for transmitting electron emitter power from a power source to the x-ray source across an insulating gap while allowing the source of the emitter power to remain at a safe potential with respect to the ambient;
   d) an x-ray transmissive window in the penetrometer pipe, said x-ray transmissive window having a metal impurity content of less than 300 ppm and a yield strength sufficiently great to withstand 250 $lb/in^2$ force on a ¼ inch diameter window; and
   e) a detector employing a solid state electrical diode for detecting returning x-rays transmitted through said x-ray transmissive window and for generating an electrical signal pulse for each x-ray whose amplitude is proportional to the energy of the x-rays.

2. A cone penetrometer according to claim 1, wherein the x-ray transmissive window is made of a material with an atomic number of 6 or below.

3. A cone penetrometer according to claim 2, wherein the x-ray transmissive window is made of boron carbide.

4. A cone penetrometer according to claim 3, wherein the boron carbide is manufactured using a hot-press method without any addition of sintering aids.

5. A cone penetrometer according to claim 3, wherein the boron carbide which is made by the hotpress method is selected on the basis of impurity content to achieve the required yield strength without exceeding the maximum level of iron or other metal impurities.

6. A cone penetrometer according to claim 1, further comprising a holder for the x-ray transmissive window that withstands the pressures from the soil or sediment displacement, and does not produce signals that interfere with said in situ analysis.

7. A cone penetrometer according to claim 1, wherein the holder for the x-ray transmissive window is made of molybdenum.

8. A cone penetrometer according to claim 1, wherein the detector is capable of resolving x-rays which have an energy difference of less than about 300 electron volts.

9. A cone penetrometer according to claim 1, wherein the miniature x-ray tube emits x-rays within 0.150 inch from the end of the x-ray tube.

10. A cone penetrometer according to claim 1, wherein the miniature x-ray tube emits x-rays at an angle of about 17 degrees from the normal to the longitudinal axis of the pipe.

11. A system for real time in situ analysis of soil or sediment by x-ray fluorescence spectroscopy comprising:
   a) a cone penetrometer according to claim 1;
   b) an x-ray power supply supplying power to the x-ray source; and
   c) an analyzer which quantitatively analyzes said electrical signal pulses generated by the detector.

12. A system according to claim 11, wherein the analyzer
   a) separates the pulses from the x-ray detector corresponding to each individual x-ray and establishes the correspondence between pulse height and energy of the x-ray;
   b) converts the pulses from the x-ray detector into a spectrum of x-rays as a function of energy by multi-channel analysis; and
   c) separates the x-rays emitted by the metals in the soil or sediment from the remainder of the spectrum, quantifies said x-rays, relates this quantity to the concentration of metals in the soil or sediment with reference to known calibration samples and displays the results for an operator.

13. A system according to claim 12, wherein the analyzer further provides necessary voltages and currents for proper detector operation.

14. A system for real time in situ analysis of soil or sediment by x-ray fluorescence spectroscopy comprising:
   a) a cone penetrometer according to claim 1;
   b) an x-ray power supply supplying power to the x-ray source; and
   c) quantitative analytical means for the detected x-rays.

15. A system according to claim 14, wherein the quantitative analytical means comprises
   a) electronic means for the detector to separate the pulses from the x-ray detector corresponding to each individual x-ray and to establish the correspondence between pulse height and energy of the x-ray;
   b) a multichannel analyzer means for converting the pulses from the x-ray detector into a spectrum of x-rays as a function of energy;
   c) spectrum analysis and display means for separating the x-rays emitted by the metals in the soil or sediment from the remainder of the spectrum, quantifying said x-rays, and relating this quantity to the concentration of metals in the soil or sediment with reference to known calibration samples and display of the results for an operator.

16. A system according to claim 15, wherein the electronic means for the detector has further means for providing necessary voltages and currents for proper detector operation.

17. A method for in situ analysis of soil or sediment by x-ray fluorescence spectroscopy comprising:
   a) inserting a cone penetrometer according to claim 1 into soil or sediment to be analyzed below the surface;
   b) applying power to the x-ray source to generate x-rays which pass out through the x-ray transmissive window and cause x-rays to return back through the window;
   c) detecting the returning x-rays with a detector in the penetrometer and transmitting the signal to above the surface; and
   d) quantitatively analyzing the detected x-rays to determine the concentration of metals in the soil.

18. A method according to claim 17, wherein the x-ray transmissive window is made of boron carbide.

* * * * *